US010386540B2

(12) United States Patent
Sato

(10) Patent No.: US 10,386,540 B2
(45) Date of Patent: Aug. 20, 2019

(54) ULTRAVIOLET MEASUREMENT SYSTEM

(71) Applicant: SEIKO EPSON CORPORATION, Tokyo (JP)

(72) Inventor: Reiko Sato, Azumino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 15/854,396

(22) Filed: Dec. 26, 2017

(65) Prior Publication Data
US 2018/0188416 A1 Jul. 5, 2018

(30) Foreign Application Priority Data
Jan. 5, 2017 (JP) .................... 2017-000775

(51) Int. Cl.
*G01W 1/02* (2006.01)
*G01J 1/02* (2006.01)
*A61B 5/00* (2006.01)
*G01J 1/42* (2006.01)
*G01J 1/44* (2006.01)

(52) U.S. Cl.
CPC ............ *G01W 1/02* (2013.01); *A61B 5/441* (2013.01); *G01J 1/0219* (2013.01); *G01J 1/0233* (2013.01); *G01J 1/0247* (2013.01); *G01J 1/429* (2013.01); *G01J 1/44* (2013.01)

(58) Field of Classification Search
CPC ....... A61B 5/441; A61B 5/411; A61B 5/6898; A61B 5/1112; A61B 5/681; A61B 5/0022; A61B 2560/0242; A61B 5/1118; G01J 1/429; G01J 1/0219; G01J 1/0233; G01J 1/0247; G01J 1/44; G01W 1/02
See application file for complete search history.

(56) References Cited

U.S. PATENT DOCUMENTS 9,068,887 B1    6/2015  Bennouri et al.
2002/0115926 A1 8/2002  Takada
(Continued)

FOREIGN PATENT DOCUMENTS

JP    2001-324582 A    11/2001
JP    2002-358590 A    12/2002
(Continued)

*Primary Examiner* — David P Porta
*Assistant Examiner* — Fani Boosalis
(74) *Attorney, Agent, or Firm* — Oliff PLC

(57) ABSTRACT

An ultraviolet measurement system includes a measurement device that is configured to be portable by a user, and measures ultraviolet information regarding an ultraviolet ray, and a display device that can perform communication with the measurement device, in which one of the measurement device and the display device includes a position acquisition unit that acquires position information indicating a position of either of the user and the measurement device, and a storage unit that stores the ultraviolet information measured by the measurement device in correlation with measurement position information which is position information of when the ultraviolet information is measured by the measurement device among pieces of position information acquired by the position acquisition unit, and in which the display device displays information based on the ultraviolet information and the measurement position information.

13 Claims, 11 Drawing Sheets

(56) References Cited

U.S. PATENT DOCUMENTS

| | | | |
|---|---|---|---|
| 2012/0326046 A1* | 12/2012 | Aslam | G01J 1/0233 |
| | | | 250/372 |
| 2013/0033970 A1 | 2/2013 | Miyake | |
| 2016/0199000 A1* | 7/2016 | Gimenez | G01J 1/0271 |
| | | | 315/151 |
| 2016/0271280 A1 | 9/2016 | Liao et al. | |
| 2017/0011210 A1* | 1/2017 | Cheong | H04W 12/06 |
| 2017/0294174 A1* | 10/2017 | Albadawi | G06F 1/163 |

FOREIGN PATENT DOCUMENTS

| | | |
|---|---|---|
| JP | 2004-205524 A | 7/2004 |
| JP | 2006-071582 A | 3/2006 |
| JP | 2009-027471 A | 2/2009 |
| JP | 2013-032919 A | 2/2013 |

\* cited by examiner

ULTRAVIOLET MEASUREMENT SYSTEM

CROSS-REFERENCE TO RELATED APPLICATION

This application claims priority of Japanese Patent Application No. 2017-000775, filed Jan. 5, 2017, which is expressly incorporated herein by reference thereto in its entirety.

BACKGROUND

1. Technical Field

The present invention relates to an ultraviolet measurement system.

2. Related Art

In the related art, there is a pointer type timepiece (so-called analog timepiece) including a dial provided with time display scales, a plurality of pointers such as an hour hand, a minute hand, and a second hand, and a drive portion driving the plurality of pointers. As such a pointer type timepiece, there is an electronic wristwatch which has a plurality of sensors built thereinto, and displays detection results in the plurality of sensors with the pointers (for example, refer to JP-A-2013-32919).

The electronic wristwatch disclosed in JP-A-2013-32919 includes sensors measuring an azimuth, pressure (atmospheric pressure), and a temperature (atmospheric temperature), and is configured to be able to display measurement results in the sensors with pointers and function hands.

In recent years, dangers of ultraviolet rays have been drawing attention since ultraviolet rays reaching the ground have been increased due to environmental changes. For example, it has become clear that, if a person is exposed to ultraviolet rays, the person is more likely to be affected with diseases such as skin cancer and cataract.

In light of these circumstances, there is an increasing demand for a configuration in which, for example, a user can understand the intensity of ultraviolet rays to which the user is exposed or a position where the user is exposed to ultraviolet rays with high intensity in order to take an effective ultraviolet-ray countermeasure.

SUMMARY

An advantage of some aspects of the invention is to provide an ultraviolet measurement system capable of understanding ultraviolet information and a measurement position of the ultraviolet information.

An ultraviolet measurement system according to an aspect of the invention includes a measurement device that is configured to be portable by a user, and measures ultraviolet information regarding an ultraviolet ray; and a display device that can perform communication with the measurement device, in which one of the measurement device and the display device includes a position acquisition unit that acquires position information indicating a position of either of the user and the measurement device, and a storage unit that stores the ultraviolet information measured by the measurement device in correlation with measurement position information which is position information of when the ultraviolet information is measured by the measurement device among pieces of position information acquired by the position acquisition unit, and in which the display device displays information based on the ultraviolet information and the measurement position information.

The term "portable by a user" includes not only a case where the measurement device can be directly mounted on a user but also a case where the measurement device is attachable to an object mounted on or carried by the user.

According to the aspect of the invention, since the measurement device is configured to be portable by a user, and is thus attached to a position to which an ultraviolet ray is directly incident, so that it is possible to more accurately measure ultraviolet information (for example, an ultraviolet amount or an ultraviolet intensity) regarding an ultraviolet ray to which the user is exposed.

The storage unit stores ultraviolet information and measurement position information which is position information of when the ultraviolet information is measured in correlation with each other, and the display device displays information based on the ultraviolet information and the measurement position information. Consequently, a user can understand at least one of the ultraviolet information and the measurement position information, and can also understand the ultraviolet information and the measurement position of the ultraviolet information in correlation with each other, by checking the display content of the display device. Therefore, since a user can understand a measurement position where ultraviolet information with a high degree of danger is measured, it is possible to take measures such as avoiding the measurement position.

In the aspect of the invention, it is preferable that the display device displays an image in which display corresponding to the ultraviolet information measured at a measurement position is set at a position corresponding to the measurement position in a map including the measurement position indicated by the measurement position information.

According to this configuration, it is possible to easily understand the measurement position by checking the map. Therefore, it is possible to more appropriately achieve the effects and also to improve convenience of the ultraviolet measurement system.

In the aspect of the invention, it is preferable that the display set in the image is a marker which differs depending on a numerical value indicated by the ultraviolet information.

According to this configuration, it is possible to promptly understand a numerical value indicated by ultraviolet information and a measurement position by checking the map. Therefore, it is possible to further improve convenience of the ultraviolet measurement system.

In the aspect of the invention, it is preferable that the storage unit stores the ultraviolet information and the measurement position information in correlation with each other in a case where a numerical value indicated by the ultraviolet information is equal to or greater than a storage threshold value.

Such ultraviolet information may be, for example, information including an ultraviolet intensity (ultraviolet illuminance) or an UV index.

According to this configuration, ultraviolet information and measurement position information are stored in a case where a numerical value indicated by the ultraviolet information is equal to or greater than the storage threshold value. Consequently, the information can be reliably stored even in a storage unit with a small storage capacity. For example, in a case where the display device includes the storage unit, and the measurement device transmits ultraviolet information to the display device if a numerical value indicated by the measured ultraviolet information is equal to or greater than the storage threshold value, it is possible to reduce a communication amount and a communication frequency between the measurement device and the display device.

In the aspect of the invention, it is preferable that the ultraviolet measurement system further includes a notification device that sends a notification to the user in a case where a numerical value indicated by the ultraviolet information is equal to or greater than a notification threshold value.

Here, an ultraviolet ray with high ultraviolet intensity may cause aging such as spots and bags, and may also cause diseases and symptoms such as skin cancer, cataract, and immune depression.

With respect thereto, according to the configuration, in a case where a numerical value indicated by the ultraviolet information is equal to or greater than the notification threshold value, the notification device sends a notification to a user, and thus it is possible to prompt the user to take ultraviolet-ray countermeasures such as wearing a cap. Therefore, it is possible to increase convenience of the ultraviolet measurement system.

In the aspect of the invention, it is preferable that the notification device continuously sends the notification to the user in a case where a period in which the numerical value is equal to or greater than the notification threshold value is a predetermined period or more.

Here, as an ultraviolet ray exposure time increases, aging progresses or an onset risk of the diseases or the symptoms is heightened.

With respect thereto, according to the configuration, since the notification is continuously sent in a case where a period in which the numerical value is equal to or greater than the notification threshold value is a predetermined period or more, the user can easily recognize that the onset risk increases. Therefore, it is possible to further improve convenience of the ultraviolet measurement system.

In the aspect of the invention, it is preferable that the notification device is mounted on a wearable apparatus which is mountable on the user, and sends the notification to the user by using vibration.

The wearable apparatus means an apparatus such as a wristwatch which is mountable on or portable by a user.

According to this configuration, a user can easily recognize the notification. Particularly, if the notification is performed by using vibration, a user carrying or wearing the wearable apparatus can easily recognize the notification.

In the aspect of the invention, it is preferable that the display device has a pointer indicating a numerical value indicated by the ultraviolet information.

According to this configuration, a user can easily and promptly understand ultraviolet information.

In the aspect of the invention, it is preferable that the display device has a dial pointed out by the pointer, and the pointer points out portions opposite to each other in the dial in a case where a numerical value indicated by the ultraviolet information indicates that the degree of danger to the user is high and a case where a numerical value indicated by the ultraviolet information indicates that the degree of danger to the user is low.

According to this configuration, it is possible to more intuitively understand the degree of danger of ultraviolet rays.

In the aspect of the invention, it is preferable that the display device includes a timepiece that is configured to be able to perform communication with the measurement device, and is mountable on the user, and the timepiece has the pointer.

According to this configuration, the timepiece which is mounted on and is used by a user has the pointer, and thus the user can easily and promptly understand a numerical value of ultraviolet information indicated by the pointer.

In the aspect of the invention, it is preferable that the display device includes the position acquisition unit and the storage unit.

According to this configuration, it is possible to easily secure a sufficient drive time for the position acquisition unit and the storage unit or a sufficient storage capacity thereof. Therefore, it is possible to easily configure the ultraviolet measurement system of the aspect of the invention.

An ultraviolet measurement system according to an aspect of the invention includes a measurement device that is configured to be portable by a user, and measures ultraviolet information regarding an ultraviolet ray; a position acquisition device that acquires position information indicating a position of either of the user and the measurement device; a storage device that stores the ultraviolet information measured by the measurement device in correlation with measurement position information which is position information of when the ultraviolet information is measured by the measurement device among pieces of position information acquired by the position acquisition device; and a display device that displays information based on the ultraviolet information and the measurement position information.

The measurement device, the position acquisition device, the storage device, and the display device may be separate devices, and two or three of the devices may be incorporated into a single apparatus.

According to the aspect of the invention, it is possible to achieve the same effects as in the above-described ultraviolet measurement system.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Hereinafter, a first embodiment of the invention will be described with reference to the drawings.

Schematic Configuration of Ultraviolet Measurement System

Figure 1:
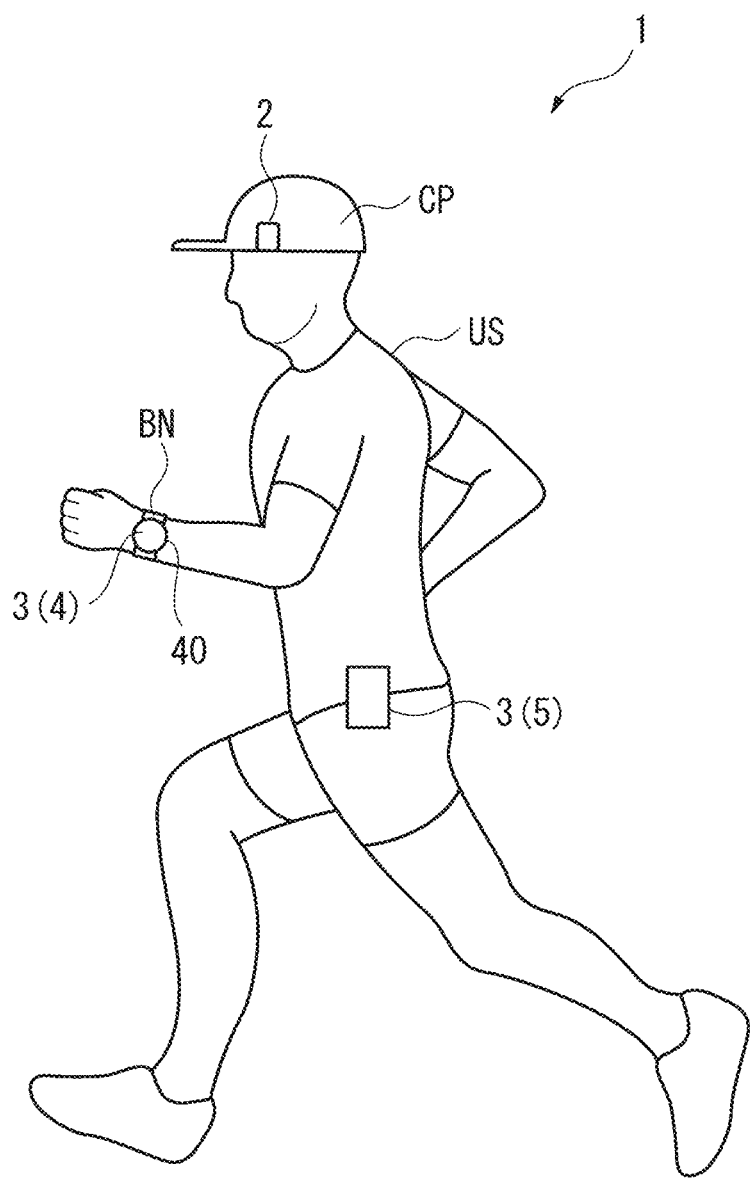
FIG. 1 is a schematic diagram illustrating a configuration of an ultraviolet measurement system according to a first embodiment of the invention.

FIG. 1 is a schematic diagram illustrating a configuration of an ultraviolet measurement system 1 according to the present embodiment.

The ultraviolet measurement system 1 (hereinafter, simply referred to as a measurement system 1 in some cases) according to the present embodiment includes, as illustrated in FIG. 1, a measurement apparatus 2 which detects ultraviolet rays, and measures ultraviolet information regarding the intensity of the ultraviolet rays, and an external apparatus 3 which is configured to be able to communicate with the measurement apparatus 2. In the present embodiment, a timepiece 4 which is a wearable apparatus mounted on a user and is used, and an information terminal 5 which records ultraviolet information measured by the measurement apparatus 2 and position information regarding a measurement position are included as the external apparatus 3.

The ultraviolet measurement system 1 has one of features in that the entire system stores measured ultraviolet information and position information indicating a measurement position (a position of the measurement apparatus 2 when the ultraviolet information is measured) of the ultraviolet information in correlation with each other, and displays the ultraviolet information and the position information.

Hereinafter, each configuration of the ultraviolet measurement system 1 will be described. In the following description, the description will be made assuming that the measurement system 1 includes not only the measurement apparatus 2 but also both of the timepiece 4 and the information terminal 5 as the external apparatuses 3. However, the measurement system 1 may include either one of the timepiece 4 and the information terminal 5 as the external apparatus 3, and is not necessarily required to include both of the timepiece 4 and the information terminal 5.

Configuration of Measurement Apparatus

Figure 2:
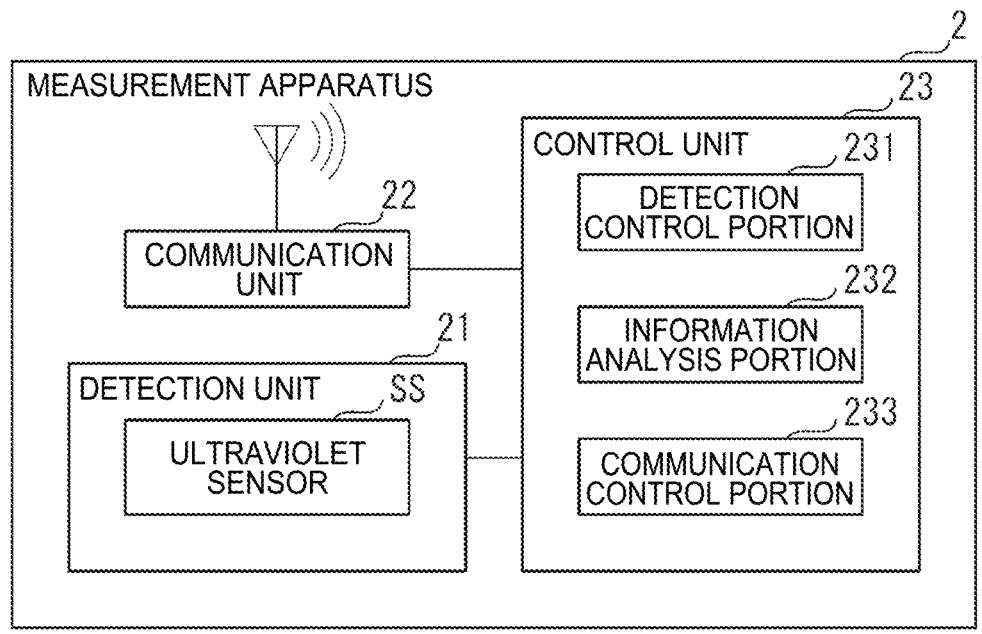
FIG. 2 is a block diagram illustrating a configuration of a measurement apparatus in the first embodiment.

FIG. 2 is a block diagram illustrating a configuration of the measurement apparatus 2.

The measurement apparatus 2 is configured to be portable by a user, and is mounted on a cap CP worn by the user and is used in an example illustrated in FIG. 1. The measurement apparatus 2 detects ultraviolet rays so as to measure and generate ultraviolet information, and transmits the generated ultraviolet information. As illustrated in FIG. 2, the measurement apparatus 2 includes a detection unit 21, a communication unit 22, and a control unit 23.

The term "portable" in the measurement apparatus 2 includes not only a case where the measurement apparatus 2 can be directly mounted on a user but also a case where the measurement apparatus 2 is attachable to an object mounted on or carried by the user. Particularly, in the present embodiment, the measurement apparatus 2 measures ultraviolet information, and thus at least a part thereof is preferably exposed to the outside while using it.

The detection unit 21 is configured to include an ultraviolet sensor SS detecting ultraviolet rays. The ultraviolet sensor SS is configured to be able to detect an ultraviolet A (UV-A) which is a long wavelength ultraviolet ray, and an ultraviolet B (UV-B) which is an intermediate wavelength ultraviolet ray in the present embodiment. However, this is only an example, and the ultraviolet sensor SS may be configured to be able to detect an ultraviolet C (UV-C) which is a short wavelength ultraviolet ray, and may be configured to be able to detect all ultraviolet rays including the ultraviolet rays. The detection unit 21 outputs a detection signal indicating a detection result in the ultraviolet sensor SS to the control unit 23.

The communication unit 22 performs communication with the external apparatus 3, and transmits and receives information to and from the external apparatus 3. The communication unit 22 may be formed of a communication module which can perform communication with an external apparatus according to a communication method based on a short-range radio communication standard such as IEEE802.15 or a communication method based on a communication standard IEEE802.16 and Long Term Evolution (LTE). The former communication method may include Bluetooth (registered trademark), and, in the present embodiment, communication between the communication unit 22 and the external apparatus 3 is performed according to Bluetooth.

The control unit 23 is configured to include a control circuit such as a central processing unit (CPU), and controls an operation of the entire measurement apparatus 2. The control unit 23 includes a detection control portion 231, an information analysis portion 232, and a communication control portion 233.

The detection control portion 231 controls an operation of the detection unit 21. The detection control portion 231 causes the detection unit 21 to detect an ultraviolet ray every predetermined time. The predetermined time is ten minutes in the present embodiment, but the predetermined time may be changed as appropriate, and the detection unit 21 may normally detect an ultraviolet ray if there is no problem in terms of drive power or the like of the measurement apparatus 2.

The information analysis portion 232 forms an ultraviolet information measurement unit along with the detection unit 21. If the detection signal is input from the detection unit 21, the information analysis portion 232 analyzes the detection signal so as to generate ultraviolet information regarding the intensity of the detected ultraviolet ray. Specifically, the information analysis portion 232 calculates the ultraviolet intensity (ultraviolet illuminance; the unit thereof is "mW/$cm^2$") on the basis of the detection signal, and also calculates an ultraviolet index (UV index) on the basis of the calculated ultraviolet intensity. The information analysis portion 232 generates ultraviolet information including numerical values of the ultraviolet intensity and the UV index. The UV index can be calculated according to a well-known computation method, and thus a detailed description thereof will be omitted.

The communication control portion 233 controls the communication unit 22 to establish communication with the external apparatus 3. If the ultraviolet information is generated by the information analysis portion 232, the communication control portion 233 transmits the ultraviolet information to the external apparatus 3 with which communication is established.

The communication control portion 233 transmits the same ultraviolet information to the external apparatuses 3 such as the timepiece 4 and the information terminal 5. However, this is only an example, and the communication control portion 233 may transmit information including a numerical value of the UV index to the timepiece 4 as ultraviolet information, and may transmit information including numerical values of the ultraviolet intensity and the UV index to the information terminal 5 as ultraviolet information. In other words, ultraviolet information transmitted to and used by the timepiece 4 and the information terminal 5 may differ in the content thereof.

Configuration of Timepiece

The timepiece 4 which is the external apparatus 3 is a wearable apparatus which is mounted on or carried by a user, and is used. The timepiece 4 displays the time, and also functions as a display device displaying the ultraviolet information acquired from the measurement apparatus 2. In a case where a numerical value of the UV index is equal to or greater than a predetermined value, the timepiece 4 also functions as a notification device which notifies a user of the fact.

As illustrated in FIG. 1, the timepiece 4 includes a timepiece main body 40 and a band BN used to mount the timepiece main body 40 on the body (for example, the wrist) of the user.

Figure 3:
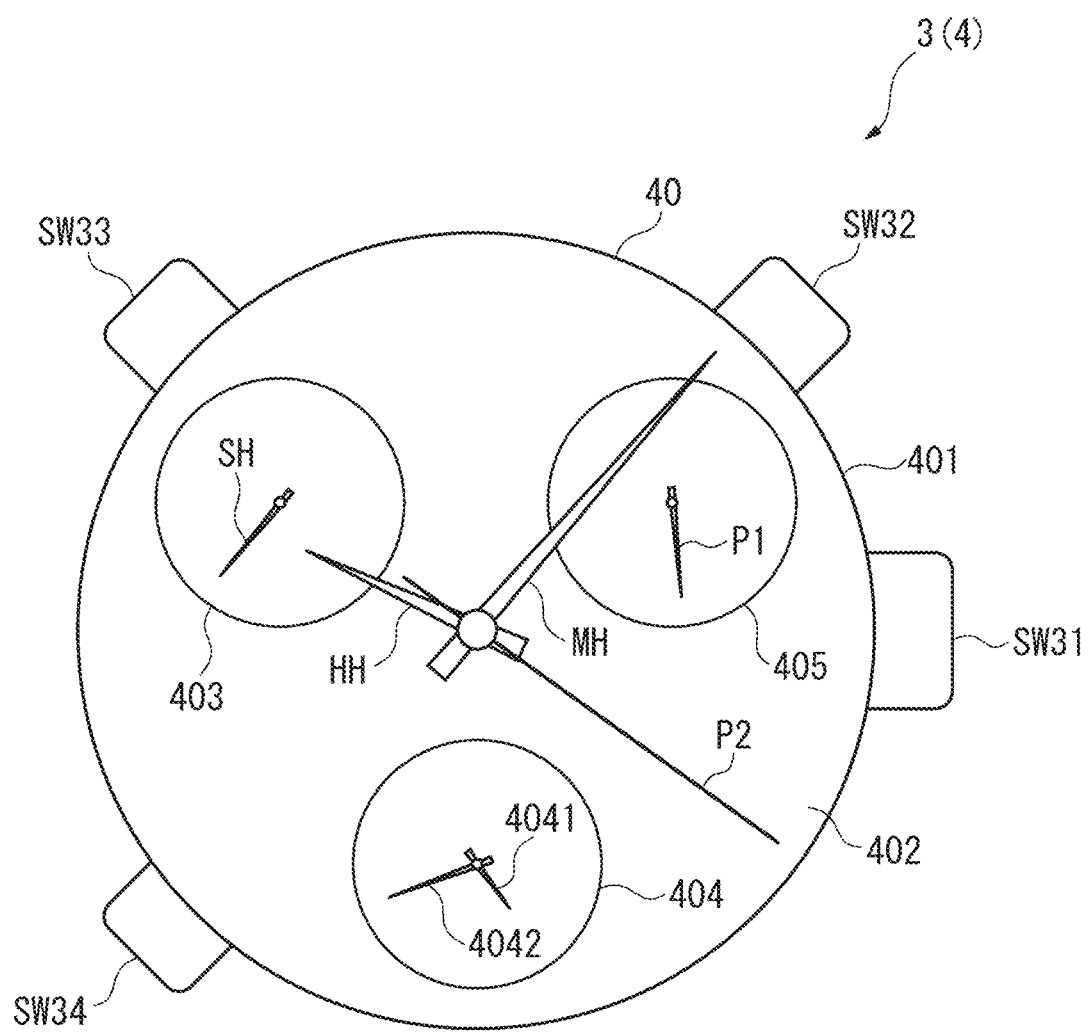
FIG. 3 is a schematic diagram illustrating a timepiece in the first embodiment.

FIG. 3 is a schematic diagram illustrating the timepiece 4.

The timepiece main body 40 includes, as illustrated in FIG. 3, a casing 401 which is a substantially circular shape in a front view, a circular dial 402 provided in the casing 401, an hour hand HH, a minute hand MH, a second hand SH, small windows 403 to 405, a pointer P1, a function hand P2, and switches SW31 to SW34.

The hour hand HH and the minute hand MH are rotatably provided such that the respective rotation axes thereof are the same as each other substantially at the center of the dial 402. The second hand SH is rotatably provided in the small window 403 disposed substantially in the ten o'clock direction in the dial 402. Rotation of the hour hand HH, the minute hand MH, and the second hand SH is controlled by a display control portion 498 (refer to FIG. 4) which will be described later.

The small window 404 is disposed substantially in the six o'clock direction in the dial 402. A mode display hand 4041 and a battery residual quantity display hand 4042 are rotatably disposed in the small window 404 such that the respective rotation axes thereof are the same as each other. Rotation of the hands 4041 and 4042 is controlled by the display control portion 498 (refer to FIG. 4).

The small window 405 is disposed substantially in the two o'clock direction in the dial 402. The pointer P1 is rotatably disposed in the small window 405. The function hand P2 is rotatably disposed in the dial 402 such that a rotation axis thereof is the same as those of the hour hand HH and the minute hand MH. Rotation of the pointer P1 and the function hand P2 is controlled by the display control portion 498 (refer to FIG. 4).

The switches SW31 to SW34 are provided to be able to project and recede on a side surface of the casing 401.

The switch SW31 is located in the three o'clock direction in the casing 401, and is a switch pressed when communication connection with the measurement apparatus 2 is established.

The switch SW32 is located in the two o'clock direction in the casing 401, and is a switch pressed when ultraviolet information measured by the measurement apparatus 2 is displayed.

The switch SW33 is located in the ten o'clock direction in the casing 401, and is a switch pressed when time correction is performed.

The switch SW34 is a switch pressed when an operation mode of the timepiece 4 is changed.

The switches SW31 to SW34 are pressed by the user, and thus output control signals corresponding to the switches to a control unit 49 which will be described later.

Internal Configuration of Timepiece

Figure 4:
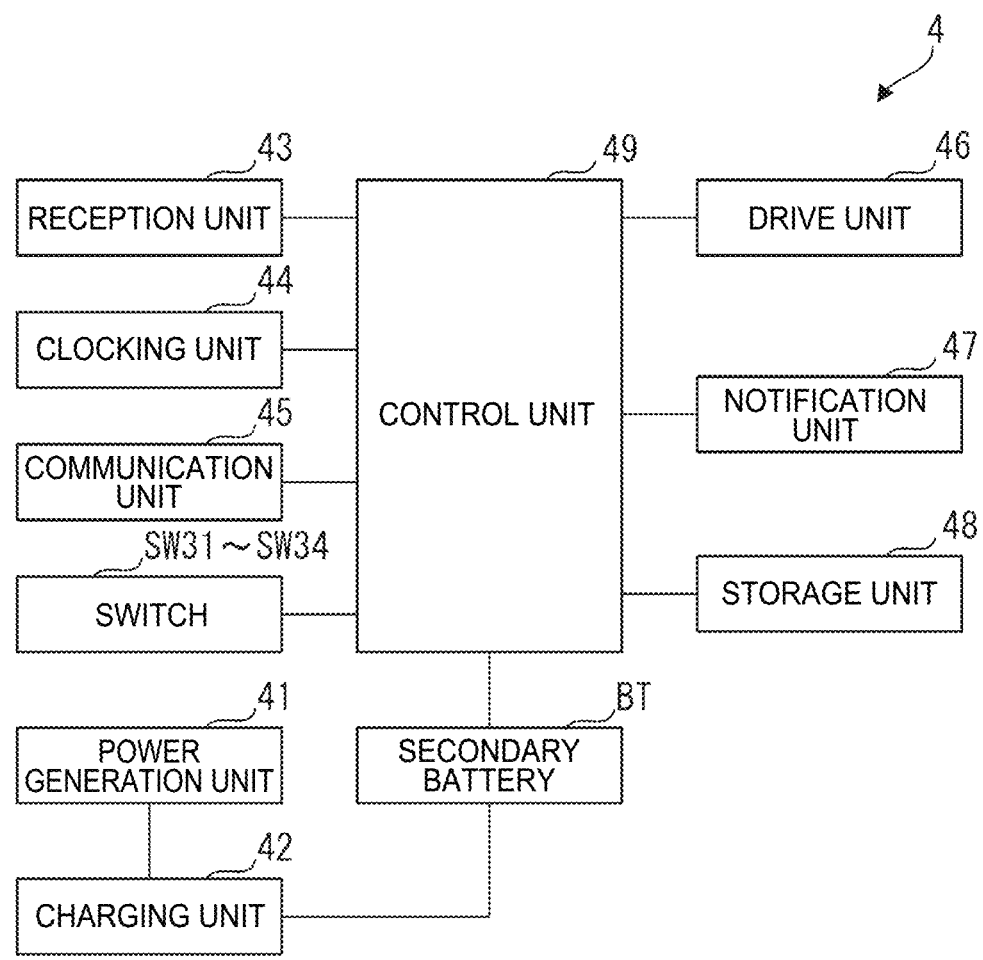
FIG. 4 is a block diagram illustrating a configuration of the timepiece in the first embodiment.

FIG. 4 is a block diagram illustrating a configuration of the timepiece 4.

In addition to the above-described configuration, as illustrated in FIG. 4, the timepiece 4 includes a power generation unit 41, a charging unit 42, a secondary battery BT, a reception unit 43, a clocking unit 44, a communication unit 45, a drive unit 46, a notification unit 47, a storage unit 48, and the control unit 49.

The power generation unit 41 is configured to include a solar cell plate provided with a plurality of solar cells (photovoltaic elements) which convert light energy into electrical energy (power). However, any other configuration may be used, and there may be a configuration in which the power generation unit 41 generates power as a result of a rotation weight rotating.

The charging unit 42 charges the secondary battery BT by using power generated by the power generation unit 41. The charging unit 42 may charge the secondary battery BT by using power supplied from the outside.

The secondary battery BT supplies drive power to the timepiece main body 40.

If a control signal is output from the switch SW33, the reception unit 43 receives present date-and-time information included in a satellite signal such as a global positioning system (GPS) signal or a standard electric wave under the control of the control unit 49.

The clocking unit 44 measures the present date and time. The present date and time are corrected by the control unit 49 on the basis of the present date-and-time information acquired by the reception unit 43.

The communication unit 45 performs communication with the measurement apparatus 2 under the control of the control unit 49 which will be described later, and receives the ultraviolet information from the measurement apparatus 2. The communication unit 45 may have the same configuration as that of the communication unit 22.

The drive unit 46 rotates (moves) the hands HH, MH, SH, 4041, 4042, P1 and P2 under the control of the control unit 49. In the present embodiment, the drive unit 46 is provided according to each hand, and is configured to include stepping motors which are driven according to pulse signals which are input from the control unit 49. However, any other configuration may be used, and there may be a configuration in which the drive unit 46 includes an actuator such as a piezoelectric element.

The notification unit 47 performs a notification of predetermined information, and is configured to include a vibration generation device generating vibration with a motor or the like in the present embodiment. However, any other configuration may be used, and the notification unit 47 may be configured to include a sound output device which performs a notification of the predetermined information with sounds such as a warning sound or a message in addition to or instead of the vibration generation device. The content of a notification performed by the notification unit 47 will be described later in detail.

The storage unit 48 is formed of a nonvolatile memory such as a flash memory, and stores various programs or data required in an operation of the timepiece 4.

Figure 5:
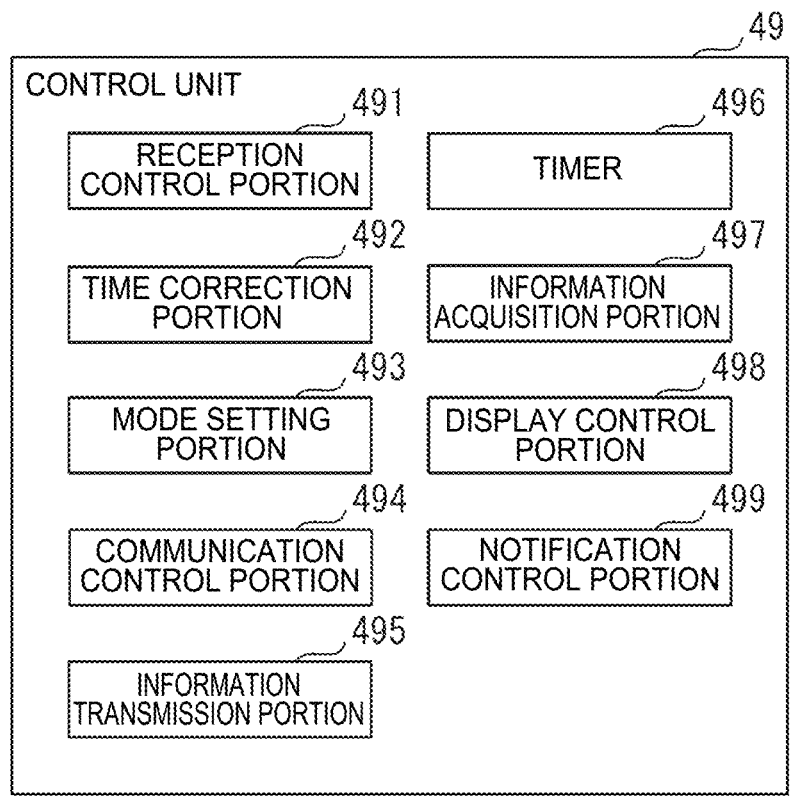
FIG. 5 is a block diagram illustrating a configuration of a control unit of the timepiece in the first embodiment.

FIG. 5 is a block diagram illustrating a configuration of the control unit 49.

The control unit 49 is configured to include a control circuit, and controls an operation of the entire timepiece 4.

For example, the control unit 49 performs processes corresponding to control signals which are input in response to pressing of the switches SW31 to SW34, and also corrects the present date and time or performs a hand movement process when the present date and time are displayed. As illustrated in FIG. 5, the control unit 49 includes a reception control portion 491, a time correction portion 492, a mode setting portion 493, a communication control portion 494, an information transmission portion 495, a timer 496, an information acquisition portion 497, the display control portion 498, and a notification control portion 499.

If a control signal is input from the switch SW33, the reception control portion 491 causes the reception unit 43 to receive the present date-and-time information. The reception control portion 491 may cause the present date-and-time information to be received periodically, for example, once a day even if the control signal is not input.

The time correction portion 492 corrects the present date and time measured by the clocking unit 44 if the present date-and-time information is received by the reception unit 43.

If a control signal is input from the switch SW34, the mode setting portion 493 changes an operation mode of the timepiece 4. Such an operation mode may include, for example, an airplane mode of stopping communication with external apparatuses, and a communication mode of performing communication with an apparatus such as the measurement apparatus 2. The present operation mode is indicated by the mode display hand 4041 (refer to FIG. 3).

The communication control portion 494 controls communication with an external apparatus using the communication unit 45. For example, the communication control portion 494 establishes communication with the measurement apparatus 2 and communication with the information terminal 5 using the communication unit 45, and stores connection information with the measurement apparatus 2 and the information terminal 5 in the storage unit 48. The communication control portion 494 causes various pieces of information to be transmitted and received between the measurement apparatus 2 and the information terminal 5, and the communication unit 45 on the basis of the connection information.

If a control signal is input from the switch SW32, the information transmission portion 495 transmits start information indicating that ultraviolet information generated by the measurement apparatus 2 starts to be displayed, to the measurement apparatus 2 via the communication unit 45. In a case where a time measured by the timer 496 reaches a predetermined time, or a control signal is input from the switch SW32 again, the information transmission portion 495 transmits end information indicating that display of the ultraviolet information ends, to the measurement apparatus 2.

The timer 496 counts the time after the start information is transmitted, and, if a predetermined time (five minutes in the present embodiment) elapses, the timer 496 causes the information transmission portion 495 to transmit the end information. The time counted by the timer 496 is reset if the end information is transmitted. In a case where ultraviolet information is transmitted from the measurement apparatus 2 whenever the ultraviolet information is measured, or a case where drive power for communication and hand movement is sufficiently secured, the information transmission portion 495 and the timer 496 may be omitted.

The information acquisition portion 497 acquires ultraviolet information received from the measurement apparatus 2 via the communication unit 45.

The display control portion 498 controls an operation of the drive unit 46, and thus rotates the hands HH, MH, SH, 4041, 4042, P1 and P2.

Specifically, the display control portion 498 rotates the hour hand HH, the minute hand MH, and the second hand SH according to the present date and time measured by the clocking unit 44.

The display control portion 498 causes the hands 4041 and 4042 to indicate a state of the timepiece 4. Specifically, the display control portion 498 rotates the mode display hand 4041 to indicate the present operation mode, and also rotates the battery residual quantity display hand 4042 to indicate a battery residual quantity of the secondary battery BT. The battery residual quantity may be detected on the basis of a voltage of drive power supplied from the secondary battery BT.

If ultraviolet information transmitted from the measurement apparatus 2 is acquired, the display control portion 498 rotates the pointer P1 to indicate a numerical value of the UV index included in the ultraviolet information.

Here, the UV index is an index indicating the intensity of an ultraviolet ray in order to easily understand the extent of the influence which the ultraviolet ray has on a human body. The UV index may be calculated according to a well-known computation method, and may be indicated by twelve stages such as integer values of 1 to 11 and "11+" indicating values of 11 or greater.

In the UV index, 1 or 2 indicates that the ultraviolet intensity is low, and thus a person can spend the time outdoors with an easy mind, 3 to 5 indicate that the ultraviolet intensity is moderate, and 6 and 7 indicate that the ultraviolet intensity is high. In a case where the UV index is in the range from 3 to 7, it is recommended that a person stays in the shades in the daytime as much as possible. On the other hand, in the UV index, 8 to 10 indicate that the ultraviolet intensity is very high, and 11 or greater ("11+") indicates that the ultraviolet intensity is extremely high. In a case where a numerical value of the UV index is 8 or greater, it is recommended that a person refrains from going outside in the daytime.

Figure 6:
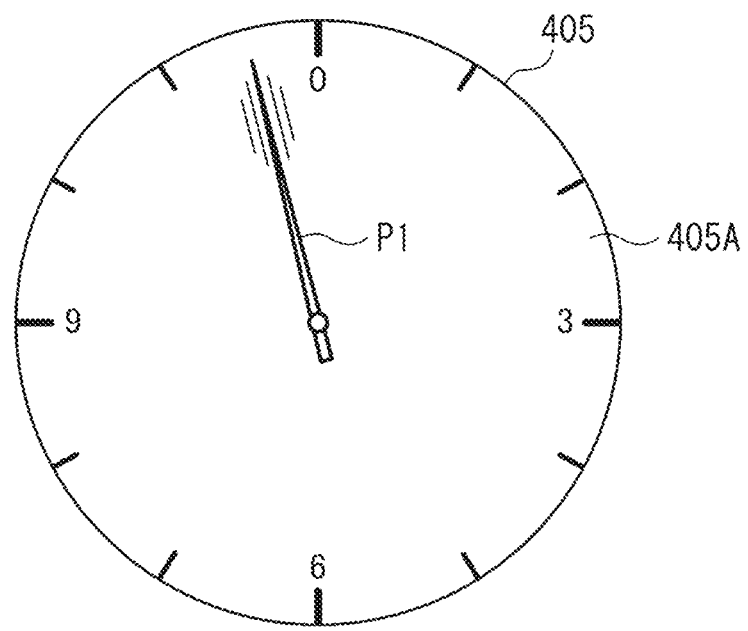
FIG. 6 is a schematic diagram illustrating a small window and a pointer in the first embodiment.

FIG. 6 is a schematic diagram illustrating the small window 405 and the pointer P1.

A numerical value of the UV index is indicated by the pointer P1. As illustrated in FIG. 6, a dial 405A of the small window 405 in which the pointer P1 is disposed is added with scales in twelve stages with the twelve o'clock direction as a starting point in a clockwise direction such that the twelve o'clock direction (the zero o'clock direction) indicates "0", the three o'clock direction indicates "3", the six o'clock direction indicates "6", and the nine o'clock direction indicates "9".

The display control portion 498 rotates the pointer P1 to a position corresponding to a numerical value of the UV index included in acquired ultraviolet information in order to indicate the numerical value. In a case where ultraviolet information is not acquired from the measurement apparatus 2, a case where an ultraviolet ray is not detected, or a case where the end information is transmitted, and display of ultraviolet information ends, the display control portion 498 locates the pointer P1 at the position of "0".

In the present embodiment, the UV index of 6 or greater indicating that the ultraviolet intensity is high is displayed by the pointer P1 indicating the scales set on the left in the small window 405. On the other hand, the UV index of 5 or smaller indicating that the ultraviolet intensity is moderate or less is displayed by the pointer P1 indicating the scales set on the right in the small window 405.

As mentioned above, the scales of the dial 405A are set such that it is possible to intuitively understand whether or not the present ultraviolet intensity has a high degree of danger to a human body on the basis of a position indicated by the pointer P1. The region of 0 to below 6 and the region of 6 or greater in the scales may be painted in different colors.

In the present embodiment, in a case where the UV index is "11+", the display control portion 498 disposes the pointer P1 between "11" and "0" in the scales as illustrated in FIG. 6, and then causes the pointer P1 to vibrate. Through such display, a user can easily understand that the present ultraviolet intensity is extremely high.

The notification control portion 499 illustrated in FIG. 5 controls the notification unit 47 to perform a notification of predetermined information.

For example, in a case where a numerical value of the acquired UV index is 8 or greater, the notification control portion 499 causes the notification unit 47 to perform a notification of attention. In a case where a period in which a numerical value of the UV index is 8 or greater is a predetermined period (for example, two minutes) or more, the notification control portion 499 causes the notification unit 47 to perform a notification of warning. In other words, in a case where a numerical value of the acquired UV index is equal to or greater than a notification threshold value or greater, the notification control portion 499 causes a notification of attention to be performed, and, in a case where a period in which a numerical value of the acquired UV index is equal to or greater than the notification threshold value or greater is a predetermined period or more, the notification control portion 499 causes a notification of warning to be performed.

In this case, for example, the notification control portion 499 generates vibration for a short period of time when the notification of attention is performed, and continuously generates vibration until a numerical value of the UV index becomes smaller than the notification threshold value or until a predetermined time elapses when the notification of warning is performed. These are only examples, and a method of performing notifications of attention and warning in the notification control portion 499 and the notification unit 47 may be changed as appropriate, and a numerical value of the notification threshold value or the predetermined period may be changed as appropriate. For example, when the notification of warning is performed, the notification control portion 499 may generate vibration at a frequency shorter than a frequency during the notification of attention, that is, vibration frequencies may be different from each other during an attention notification and a warning notification.

Configuration of Information Terminal

Figure 7:
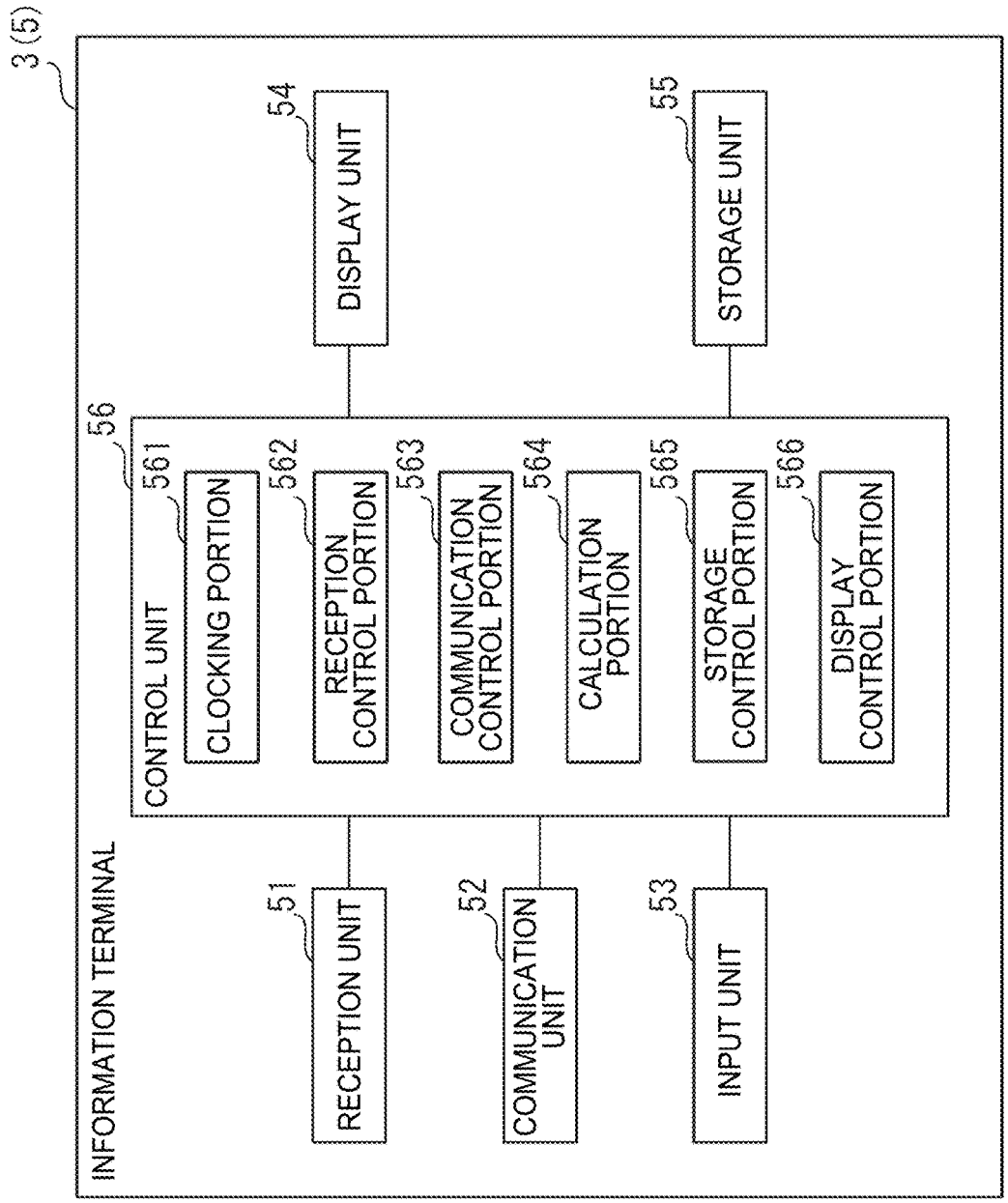
FIG. 7 is a block diagram illustrating a configuration of an information terminal in the first embodiment.

FIG. 7 is a block diagram illustrating a configuration of the information terminal 5.

As illustrated in FIG. 1, the information terminal 5 which is the external apparatus 3 is formed of a smart phone (multifunction mobile phone) which is portable by a user US in the present embodiment. The information terminal 5 records ultraviolet information which is measured by the measurement apparatus 2 and is received, and also has a function of acquiring and storing measurement position information indicating a position (measurement position) of the measurement apparatus 2 of when the ultraviolet information is measured. In other words, the information terminal 5 also functions as a position acquisition device and a storage device. The information terminal 5 also functions as a display device displaying information based on the ultraviolet information and the measurement position information.

As illustrated in FIG. 7, the information terminal 5 is configured to include a reception unit 51, a communication unit 52, an input unit 53, a display unit 54, a storage unit 55, and a control unit 56.

The reception unit 51 receives a satellite signal from a position information satellite such as the GPS so as to acquire position information indicating a position of the information terminal 5 and further positions of the measurement apparatus 2 and the user US. In other words, the reception unit 51 corresponds to a position acquisition unit according to the invention. A satellite signal received by the reception unit 51 is not limited to a satellite signal from a GPS, and may be satellite signals transmitted from satellites used for other Global Navigation Satellite Systems (GNSS) such as GLONASS (Russia), Galileo (EU), and Beidou (China). A satellite signal transmitted from a stationary satellite for Satellite-Based Augmentation System (SBAS), or a satellite signal transmitted from a satellite for Radio Navigation Satellite Service (RNSS), such as a quasi-zenith satellite which can be searched in a specific region, may be used.

In the same manner as the communication unit 45, the communication unit 52 performs communication with the measurement apparatus 2 under the control of the control unit 56 which will be described later, and receives the ultraviolet information from the measurement apparatus 2. The communication unit 52 may be formed of the same communication module as that of the communication unit 45.

The input unit 53 may be formed of physical keys provided on the information terminal 5, may also be formed of a touch panel provided according to a display surface of the display unit 54 which will be described later. The input unit 53 outputs an operation signal corresponding to the user's input operation on the physical keys and the touch panel, to the control unit 56. In a case where the information terminal 5 has a microphone, the input unit 53 may output an operation signal corresponding to a voice signal recognized by the microphone.

The display unit 54 displays an image generated by the control unit 56. The display unit 54 may be configured to include a display panel such as a liquid crystal panel or an organic electroluminescence (EL) panel. The display unit displays, for example, an operation screen of the information terminal 5, or a measurement result display screen including the ultraviolet information or the position information. The measurement result display screen will be described later in detail.

The storage unit 55 stores various programs or data required for an operation of the information terminal 5. For example, the storage unit 55 stores an operating system (OS) for operating the information terminal 5, or application programs. The storage unit 55 stores ultraviolet information acquired from the measurement apparatus 2, position information (measurement position information) of when the ultraviolet information is acquired, and date-and-time information (measurement date-and-time information) of when the ultraviolet information is measured in correlation with each other. The storage unit 55 may be formed of a non-volatile memory such as a flash memory or a recording medium such as a hard disk drive (HDD).

The control unit 56 is configured to include a control circuit such as a CPU, and controls an operation of the entire information terminal 5. For example, the control unit 56 controls the communication unit 52 so as to acquire the ultraviolet information from the measurement apparatus 2 and also to acquire measurement position information, and stores the ultraviolet information and the measurement position information (further measurement date-and-time information) in correlation with each other. The control unit 56 displays a measurement result display screen including at least the ultraviolet information on the display unit 54. The control unit 56 includes a clocking portion 561, a reception control portion 562, a communication control portion 563, a calculation portion 564, a storage control portion 565, and a display control portion 566.

The clocking portion 561 measures the present date and time.

The reception control portion 562 causes the reception unit 51 to acquire position information.

The communication control portion 563 causes the communication unit 52 to establish communication connection with the measurement apparatus 2. The communication control portion 563 receives ultraviolet information from the measurement apparatus 2.

The calculation portion 564 calculates various pieces of information on the basis of the ultraviolet information. Specifically, the calculation portion 564 calculates the maximum UV index value on the measurement day of the ultraviolet information on the basis of an UV index included in the ultraviolet information transmitted from the measurement apparatus 2, and also calculates an average UV index value in a period in which a numerical value of the UV index is 1 or greater on the measurement day. The calculation portion 564 calculates an integrated value of ultraviolet ray exposure amounts on the measurement day. In this case, since the ultraviolet sensor SS can detect the UV-A and the UV-B, the calculation portion 564 calculates an exposure amount integrated value of the UV-A and an exposure amount integrated value of the UV-B on the measurement day. In the present embodiment, the exposure amount integrated value is a temporal integrated value of ultraviolet ray exposure amounts, and the unit thereof is a minimal erythematic dose (MED), but this is only an example, a value obtained according to other computation methods may be used, and such an exposure amount integrated value may not be calculated. The calculation portion 564 may calculate the information whenever ultraviolet information is acquired from the measurement apparatus 2, and may calculate the information at a predetermined timing (for example, 0 o'clock of the next day).

The storage control portion 565 stores various pieces of information in the storage unit 55. For example, in a case where ultraviolet information is acquired by the communication control portion 563, the storage control portion 565 acquires date-and-time information at which the ultraviolet information is measured from the clocking portion 561 as measurement date-and-time information of the ultraviolet information, causes the reception control portion 562 to acquire position information as measurement position information, and stores the ultraviolet information, the measurement date-and-time information, and the measurement position information in the storage unit 55 in correlation with each other. The storage control portion 565 stores the calculation results in the calculation portion 564 in the storage unit 55 in correlation with the measurement day of the ultraviolet information which is a base of the calculation results.

The display control portion 566 is configured to include a rendering circuit such as a graphics processing unit (GPU), and draws images of various screens. For example, the display control portion 566 draws an image forming the operation screen, and generates an image forming a measurement result display screen including ultraviolet information acquired from the measurement apparatus 2. These images are displayed on the display unit 54.

Figure 8:
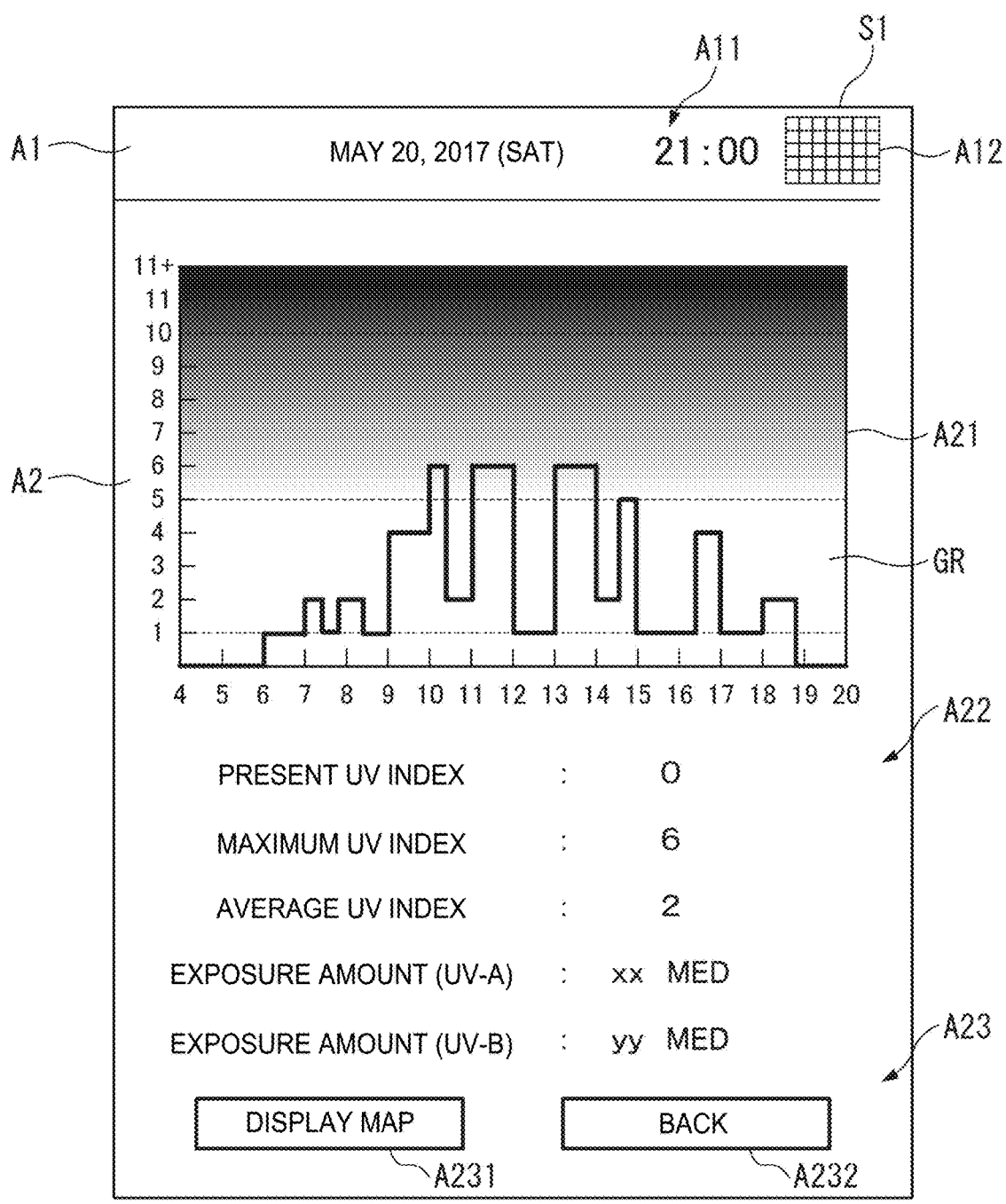
FIG. 8 is a diagram illustrating an example of a that-day information display screen in the first embodiment.
Figure 9:
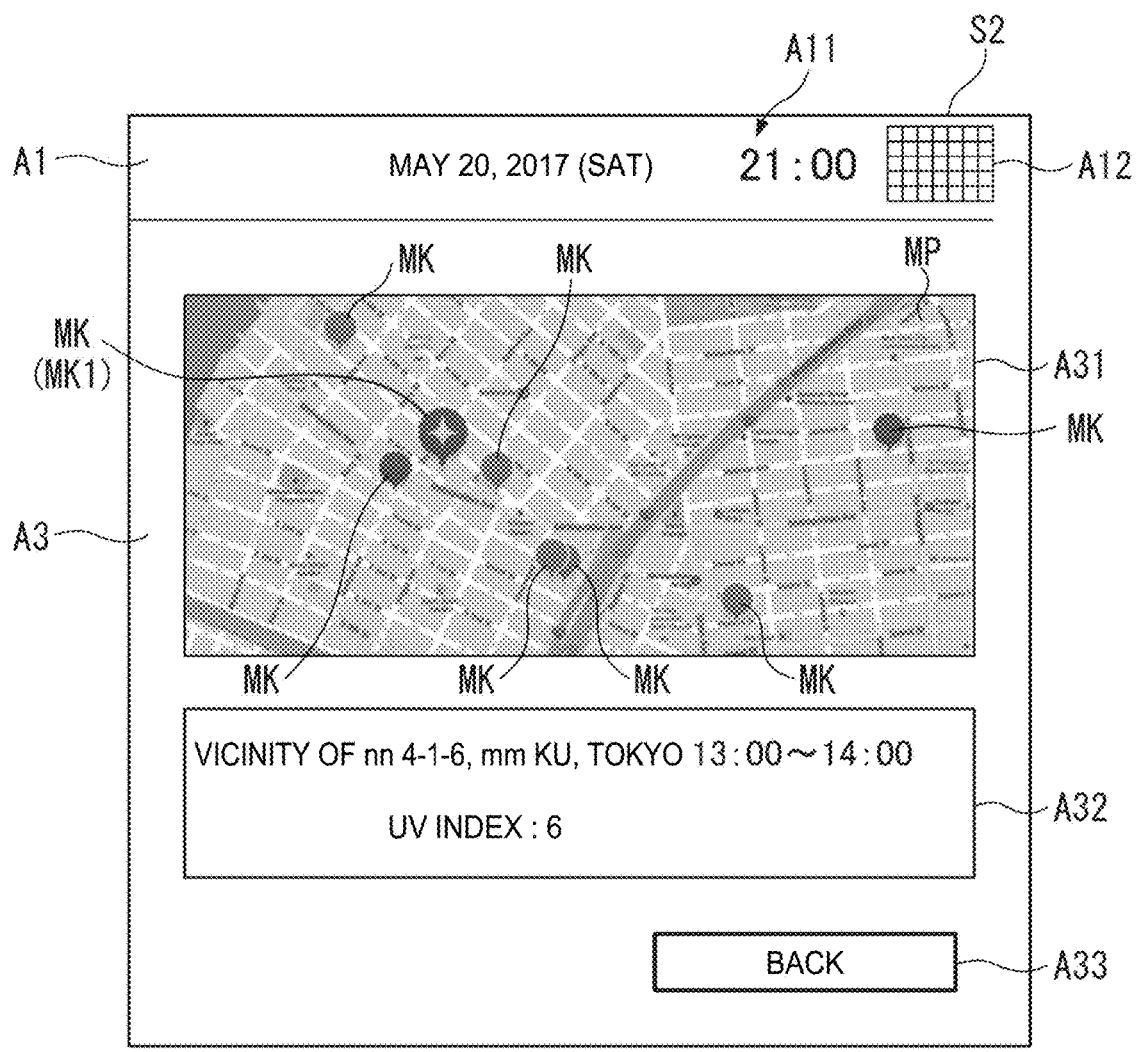
FIG. 9 is a diagram illustrating an example of a map display screen in the first embodiment.

The measurement result display screen includes a that-day information display screen S1 (refer to FIG. 8) and a map display screen S2 (refer to FIG. 9).

Example of that-Day Information Display Screen

FIG. 8 is a diagram illustrating an example of the that-day information display screen S1.

The that-day information display screen S1 is a screen on which details of ultraviolet information on the date (reference day) selected by the user can be viewed. As illustrated in FIG. 8, the that-day information display screen S1 includes a date-and-time display region A1 located on the screen upper part, and a variable display region A2 located on the screen lower part.

The date-and-time display region A1 is a region in which the reference day is displayed. A date-and-time display field A11 is located at the center, and a calendar button A12 is located in the date-and-time display region A1.

The reference day is displayed in the date-and-time display field A11. In a case where the reference day is today, the present time is also displayed as illustrated in FIG. 8.

The calendar button A12 is a button for selecting a reference day. If the calendar button A12 is pressed, a calendar from which a reference day can be selected is displayed although not illustrated. If a reference day is changed by using the calendar, the display control portion 566 generates the that-day information display screen S1 based on ultraviolet information on the reference day and the calculation results, and thus the that-day information display screen S1 on the selected reference day is displayed on the display unit 54. A reference day may be changed to the previous day and the next day by swiping the that-day information display screen S1 leftward and rightward.

The variable display region A2 is a region in which detailed data of the ultraviolet information on the reference day is displayed. The variable display region A2 includes a graph display portion A21, a data display portion A22, and a button arrangement portion A23.

A graph GR is set in the graph display portion A21. The graph GR is a graph indicating a temporal change of a numerical value of the UV index measured by the measurement apparatus 2 on the reference day, and a time is set on a transverse axis thereof, and a numerical value of the UV index is set on a longitudinal axis thereof. In the present embodiment, the transverse axis expresses the time from 4 o'clock before sunrise to 20 o'clock after sunset. However, this is only an example, and it suffices that the time from sunrise to sunset on the reference day is included in the transverse axis, and the time from 0 o'clock to 24 o'clock may be set. A gradation is set on the background of the graph GR such that the gradation increases as the UV index becomes higher, but such a gradation may be omitted.

Various pieces of information on the reference day calculated by the calculation portion 564 are set in the data display portion A22. In the present embodiment, the maximum UV index, an average UV index, an exposure amount of the UV-A, and an exposure amount of the UV-B on the reference day are set in the data display portion A22. In a case where the reference day is today, as illustrated in FIG. 8, a numerical value of the UV index (a numerical value of the present UV index) included in the latest ultraviolet information is set.

A map display button A231 and a back button A232 are disposed in the button arrangement portion A23. Of the buttons, if the map display button A231 is pressed (input), the map display screen S2 generated by the display control portion 566 is displayed, and, if the back button A232 is pressed (input), a screen which is displayed right before the that-day information display screen S1 is displayed.

By referring to the graph GR of the that-day information display screen S1, the user wearing the measurement apparatus 2 can check an intensity change of ultraviolet rays to which the user is exposed for a day. The user can check detailed ultraviolet information by checking information displayed in the data display portion A22 of the that-day information display screen S1.

Example of Map Display Screen

FIG. 9 is a diagram illustrating an example of the map display screen S2.

The map display screen S2 is a screen indicating a location where a numerical value of the UV index is greater than a predetermined threshold value in the user's action for a day. The map display screen S2 includes, as illustrated in FIG. 9, the date-and-time display region A1 and a variable display region A3, and the variable display region A3 includes a map display portion A31, a location information display portion A32, and a back button A33.

Among the buttons, if the back button A33 is pressed (input), the that-day information display screen S1 on the same reference day is displayed, and, if the map display screen S2 is swiped leftward and rightward, the map display screens S2 with the previous day and the next day as reference days are displayed.

A map MP including an action range of the user on the reference day is set in the map display portion A31. The action range is a range including a position indicated by measurement position information which is acquired and recorded when ultraviolet information is received from the measurement apparatus 2. In the map MP, a marker MK is set in a location where, among numerical values of the UV index measured on the reference day, a numerical value of the threshold value (for example, 6 indicating a high ultraviolet intensity) or greater is measured. A color is set for the marker MK for each UV index, and the color is set to become closer to red which makes the user feel danger as the UV index becomes higher. However, this is only an example, and, if a numerical value of the measured UV index is 1 or greater, the marker MK may be set in a measurement position of the UV index.

The map MP may be enlarged and reduced through operations such as pinch-out and pinch-in of the user.

If the user selects one of the markers MK on the map MP, the marker MK is changed to a marker MK1 having a shape which is different from that of the marker MK, and detailed information of a position indicated by the marker MK1 is set in the location information display portion A32.

The detailed information includes, for example, an address of the position, a stay time range at the position, and a value of the UV index at the position. Above all, the address of the position may be acquired on the basis of position information of when ultraviolet information of the position is acquired, among addresses (location names) of respective pieces of position information stored in the storage unit 55. The stay time range and the value of the UV index may be acquired on the basis of ultraviolet information and measurement position information on the reference day.

It is possible to understand a place where the highest UV index is measured in the user's action for a day by checking the map display screen S2, and thus to take measures such as avoiding the place.

The that-day information display screen S1 and the map display screen S2 are only examples, and items included in the screens S1 and S2 or a layout of the display content may be changed as appropriate.

Effects of First Embodiment

According to the measurement system 1 according to the present embodiment described above, it is possible to achieve the following effects.

The measurement apparatus 2 is configured to be portable by a user, and is thus attached to a position to which an ultraviolet ray is directly incident, so that it is possible to more accurately measure ultraviolet information regarding the intensity of an ultraviolet ray to which the user is exposed.

On the other hand, the information terminal 5 includes the reception unit 51 which is a position acquisition unit acquiring position information indicating a position of a user (in other words, a position of the measurement apparatus 2) carrying the measurement apparatus 2. The information terminal 5 includes the storage unit 55 which stores ultraviolet information acquired from the measurement apparatus 2 and measurement position information which is position information of when the ultraviolet information is measured in correlation with each other. The information terminal 5 displays a measurement result display screen which is information based on the ultraviolet information and the measurement position information. Consequently, a user can understand each of the ultraviolet information and the measurement position information individually, and can also understand the ultraviolet information and the measurement position in correlation with each other, by checking the content of the measurement result display screen. Therefore, since a user can understand a measurement position where ultraviolet information with a high degree of danger to the user is measured, it is possible to take measures such as avoiding the measurement position.

The timepiece 4 as a wearable apparatus which is mountable on a user has the pointer P1 indicating a numerical value of the UV index included in ultraviolet information acquired from the measurement apparatus 2. Consequently, the user can easily and promptly understand the numerical value of the UV index, that is, the ultraviolet intensity.

In addition thereto, the information terminal 5 functions as a position acquisition device acquiring measurement position information, a storage device storing ultraviolet information, and a display device displaying the ultraviolet information and the measurement position information. Consequently, it is possible to easily secure a sufficient drive time or storage capacity and also to easily secure a relatively large display region. Therefore, it is possible to easily configure the measurement system 1.

The information terminal 5 displays the map display screen S2 which is an image in which the marker MK corresponding to ultraviolet information measured at a measurement position is set at a position corresponding to the measurement position of ultraviolet information in the map MP. Consequently, it is possible to easily understand a measurement position of ultraviolet information. Therefore, it is possible to improve convenience of the measurement system 1.

The marker MK set in the map display screen S2 differs depending on a numerical value of the UV index included in ultraviolet information. According to this configuration, it is possible to understand both of a numerical value of the UV index (that is, ultraviolet intensity) and a measurement position by checking the map MP. Therefore, it is possible to further improve convenience of the measurement system 1.

Here, a strong ultraviolet ray may cause aging such as spots and bags, and may also cause diseases and symptoms such as skin cancer, cataract, and immune depression.

With respect thereto, in a case where a numerical value of the UV index measured by the measurement apparatus 2 is equal to or greater than a notification threshold value of attention, the timepiece 4 functions as a notification device, and notifies a user of attention via the notification unit 47. Consequently, the user US can easily take measures such as not being exposed to ultraviolet rays. Therefore, it is possible to increase convenience of the measurement system 1.

Here, as an ultraviolet ray exposure time (exposure time) increases, aging progresses or an onset risk of the diseases or the symptoms is heightened.

The timepiece 4 functioning as a notification device causes the notification unit 47 to continuously perform a notification in a case where a period in which a numerical value of the UV index is equal to or greater than the notification threshold value is longer than the predetermined period. Consequently, the user US can easily recognize that the onset risk increases. Therefore, it is possible to further improve convenience of the measurement system 1.

The notification unit 47 is mounted on the timepiece 4 as a wearable apparatus which is mountable on the user US, and the notification unit 47 performs the notifications of attention and warning by using generated vibration. Consequently, the user US wearing the timepiece 4 can easily recognize the notifications. An exterior of the timepiece 4 is not damaged since these notifications are performed by using vibration. It is possible to prevent sounds indicating attention or warning from being output to the periphery compared with a case where the notifications are performed by using the sounds.

The timepiece 4 functioning as a display device has the dial 405A of the small window 405 for performing indication with the pointer P1. The pointer P1 indicates portions opposite side to each other in a case where the UV index is 6 or greater indicating that the degree of danger to a human body is high and a case where the UV index is 5 or smaller indicating that the degree of danger to a human body is low. Consequently, it is possible to more intuitively understand the present degree of danger of ultraviolet rays.

Second Embodiment

Next, a second embodiment of the invention will be described.

An ultraviolet measurement system according to the present embodiment has the same configuration as that of the measurement system 1. Here, in the measurement system 1, the measurement apparatus 2 transmits ultraviolet information to the timepiece 4 in a case where start information is received, and transmits the ultraviolet information to the information terminal 5 whenever the ultraviolet information is measured. In contrast, in the ultraviolet measurement system according to the present embodiment, a measurement apparatus transmits the ultraviolet information to external apparatuses (a timepiece and an information terminal) in a case where a numerical value (for example, an ultraviolet intensity or a numerical value of an UV index) indicating the intensity of measured ultraviolet rays is equal to or greater than a predetermined value. In relation to this fact, the ultraviolet measurement system according to the present embodiment is different from the measurement system 1. In the following description, the same constituent elements or the substantially same constituent elements as those described above are given the same reference numerals, and description thereof will be omitted.

Schematic Configuration of Ultraviolet Measurement System

Figure 10:
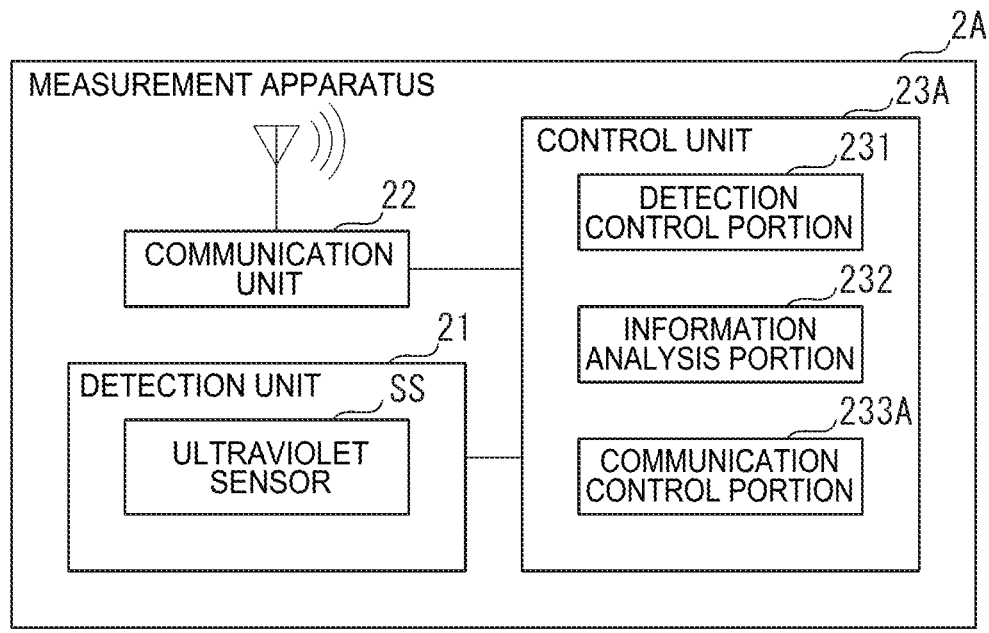
FIG. 10 is a block diagram illustrating a configuration of a measurement apparatus of an ultraviolet measurement system according to a second embodiment of the invention.
Figure 11:
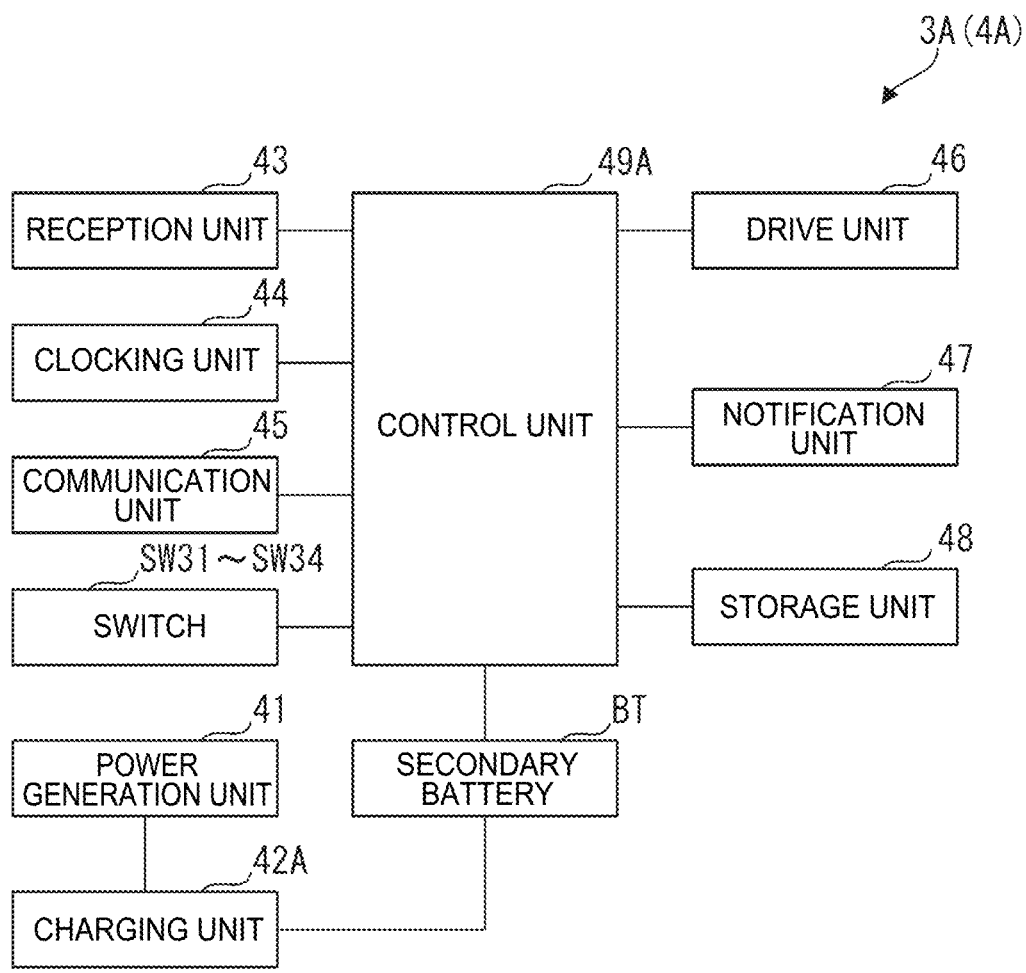
FIG. 11 is a block diagram illustrating a configuration of a timepiece in the second embodiment.

FIG. 10 is a block diagram illustrating a configuration of a measurement apparatus 2A included in an ultraviolet measurement system according to the present embodiment, and FIG. 11 is a block diagram illustrating a configuration of a timepiece 4A included in external apparatuses 3A.

As illustrated in FIGS. 10 and 11, the ultraviolet measurement system according to the present embodiment has the same configuration and function as those of the measurement system 1 except that the measurement apparatus 2A (FIG. 10) and the external apparatuses 3A including the timepiece 4A (FIG. 11) and an information terminal 5 are provided instead of the measurement apparatus 2 and the external apparatuses 3 including the timepiece 4 and the information terminal 5.

Configuration of Measurement Apparatus

The measurement apparatus 2A is configured to be portable by a user in the same manner as the measurement apparatus 2, and detect an ultraviolet ray so as to measure, generate, and transmit ultraviolet information. As illustrated in FIG. 10, the measurement apparatus 2A includes a detection unit 21 provided with an ultraviolet sensor SS, a communication unit 22, and a control unit 23A. Among the units, the control unit 23A includes a detection control portion 231 and an information analysis portion 232, and includes a communication control portion 233A instead of the communication control portion 233.

The communication control portion 233A controls the communication unit 22 to establish communication with the external apparatuses 3A in the same manner as the communication control portion 233. If the ultraviolet information is generated by the information analysis portion 232, the communication control portion 233A transmits the ultraviolet information to the external apparatuses 3A with which communication is established. In this case, the communication control portion 233A transmits the ultraviolet information to the timepiece 4A not only in a case where the start information is received but also in a case where a calculated value of the UV index is equal to or greater than a predetermined value. In a case where the calculated value of the UV index is equal to or greater than the predetermined value, the communication control portion 233A transmits the ultraviolet information to the information terminal 5.

The predetermined value may be changed as appropriate, but is set to "3" indicating that an ultraviolet intensity in the UV index is moderate in the present embodiment.

Configuration of Timepiece

The timepiece 4A included in the external apparatuses 3A is a wearable apparatus which is carried by, mounted on, and used by a user, in the same manner as the timepiece 4, displays the time, and also functions as a display device displaying the ultraviolet information acquired from the measurement apparatus 2A. As illustrated in FIG. 11, the timepiece 4A has the same configuration as that of the timepiece 4 except that a charging unit 42A and a control unit 49A are provided instead of the control unit 49.

Of the units, the charging unit 42A charges a secondary battery BT by using power generated by a power generation unit 41, and also charges the secondary battery by using power supplied from the outside.

The control unit 49A is configured to include a control circuit, and controls an operation of the entire timepiece 4A. Although not illustrated, in the same manner as the control unit 49, the control unit 49A includes a reception control portion 491, a time correction portion 492, a mode setting portion 493, a communication control portion 494, an information transmission portion 495, a timer 496, an information acquisition portion 497, a display control portion 498, and a notification control portion 499.

Among the portions, the display control portion 498 and the notification control portion 499 in the present embodiment are operated in a period from transmission of the start information in the information transmission portion 495 to transmission of the end information, and are also operated in a case where the ultraviolet information is acquired from the measurement apparatus 2A.

Specifically, in a case where the UV index is equal to or more than the predetermined value, the ultraviolet information is transmitted from the measurement apparatus 2A, and is received by the timepiece 4A.

Thus, the display control portion 498 rotates (moves) a pointer P1 according to a numerical value of the UV index included in the ultraviolet information in the same manner as after the start information is transmitted.

The notification control portion 499 causes a notification unit 47 to perform a notification of attention in a case where the above-described attention notification condition is satisfied, and causes the notification unit 47 performs a notification of warning in a case where the warning notification condition is satisfied.

According to the timepiece 4A, in a case where an ultraviolet ray with a high degree of danger is detected, the timepiece 4A mounted on a user can notify the user of the fact.

On the other hand, the information terminal 5 functions as a position acquisition device, a storage device, and a display device in the same manner as in the first embodiment. In a case where a measured UV index is equal to or more than 3, the information terminal 5 (control unit 56) receives and acquires ultraviolet information transmitted from the measurement apparatus 2A, and stores the ultraviolet information in a storage unit 55 in correlation with position information (measurement position information) and date-and-time information (measurement date-and-time information) of when the ultraviolet information is received. Various pieces of information such as the maximum UV index value are calculated on the basis of the information, and the measurement result display screen is generated and displayed by the display unit 54 (refer to FIG. 8).

Effects of Second Embodiment

According to the measurement system of the present embodiment described above, it is possible to achieve the following effects in addition to the same effects as those in the measurement system 1.

In a case where a numerical value of a measured UV index is equal to or greater than 3, the measurement apparatus 2A transmits ultraviolet information to the information terminal 5 functioning as a storage device, and the information terminal 5 stores the received and acquired ultraviolet information in correlation with measurement position information and measurement date-and-time information. In other words, in a case where a numerical value of the UV index is equal to or greater than a storage threshold value, the information terminal 5 stores the information. Consequently, even in a case where a storage capacity of the storage unit 55 of the information terminal 5 is small, the information can be reliably stored. For example, in a case where the timepiece 4A which is a wearable apparatus mounted on a user stores the information instead of the information terminal 5, a storage unit 48 of the timepiece 4A is expected to have a small storage capacity, but can reliably store the ultraviolet information and the position information even in this case.

Modification Examples of Embodiments

The invention is not limited to the embodiments, and modifications, alterations, and the like within the scope of being capable of achieving the object of the invention are included in the invention.

In each of the embodiments, the information terminal 5 functions as a position acquisition device acquiring position information indicating a position of the information terminal 5 and further a position of the measurement apparatus 2 or 2A. The information terminal 5 functions as a storage device storing ultraviolet information acquired from the measurement apparatus 2 or 2A in correlation with measurement position information. The information terminal 5 displays the measurement result display screen based on the ultraviolet information and the measurement position information. The timepiece 4 or 4A functions as a notification device performing notifications of attention and warning based on ultraviolet information, and also functions as a display device displaying the ultraviolet information. However, any other configuration may be used, and, in the measurement system, each of a measurement apparatus, a position acquisition device, a storage device, a notification device, and a display device may be a separate apparatus, and at least two thereof may be included as constituent elements forming a single device or an apparatus.

For example, in a case where the measurement apparatus 2 or 2A includes a storage device storing ultraviolet information, and the external apparatus 3 or 3A includes a position acquisition device, another storage device storing position information acquired by the position acquisition device, and a display device, and displays the measurement result display screen, the external apparatus 3 may receive ultraviolet information from the measurement apparatus 2 or 2A as necessary.

For example, in a case where the measurement apparatus 2 or 2A includes a position acquisition device, and a storage device storing position information (measurement position information) acquired by the position acquisition device when ultraviolet information is measured in correlation with the ultraviolet information, and displays the measurement result display screen, the external apparatus 3 may receive ultraviolet information and measurement position information from the measurement apparatus 2 or 2A as necessary. In this case, preferably, the measurement apparatus 2 or 2A includes a clocking unit measuring the present date and time, and the storage device stores ultraviolet information and measurement position information, and the present date and time (measurement date-and-time information) of when the information is measured and acquired. As in the information terminal 5 described in the second embodiment, when the storage device stores ultraviolet information or measurement position information, the storage device may store storage target information, for example, only in a case where a numerical value of the UV index is equal to or greater than a predetermined storage threshold value.

The timepiece 4 or 4A may include at least one of a position acquisition unit and a storage unit so as to function as a display device, and also to function as at least one of a position acquisition device and a storage device. The measurement apparatus 2 or 2A includes at least one of a position acquisition unit and a storage unit so as to function as a measurement device and also to function as at least one of a position acquisition device and a storage device.

In each of the embodiments, the external apparatuses 3 or 3A include the timepiece 4 or 4A and the information terminal 5. However, any other configuration may be used, and, the external apparatus may be, for example, a wearable apparatus such as a head mounted display, and may be other electronic apparatuses. The external apparatus may be either one of the timepiece 4 or 4A and the information terminal 5.

The timepiece 4 or 4A may not be an analog timepiece having the pointer P1, and may be a digital timepiece. In this case, for example, if a display region of a timepiece formed as a digital timepiece is relatively large, the timepiece may display the measurement result display screen (at least one of the screens S1 and S2). Even if the timepiece 4 or 4A is a digital timepiece, the pointer P1 may be displayed as an image. The information terminal 5 may have the same pointer as the pointer P1, and may display an image indicating ultraviolet information with a pointer.

There may be a configuration in which the measurement result display screen is generated by the information terminal 5 or a service (not illustrated) located on a network, and the generated measurement result display screen is displayed on an external apparatus such as a timepiece.

In each of the embodiments, ultraviolet information includes an ultraviolet intensity and a numerical value of the UV index. However, this is only an example, and the ultraviolet information may include either one of an ultraviolet intensity and an UV index, and may include other information regarding the intensity of an ultraviolet ray instead of or in addition to the ultraviolet intensity and the UV index.

In each of the embodiments, the information terminal 5 displays the map display screen S2 in which the marker MK corresponding to a numerical value of the UV index included in ultraviolet information is set in the map MP including a position (measurement position) of the measurement apparatus 2 or 2A of when the ultraviolet information is measured. However, this is only an example, and the map display screen S2 may not be displayed. For example, a screen including at least one of items of the display content included in the map display screen S2 and the that-day information display screen S1 may be displayed by an external apparatus. Even in a case where the map display screen S2 is displayed, the marker MK set on the map MP may not have a color or a shape corresponding to a numerical value of the UV index, and the markers MK having the same color or shape may be set on the map MP in a case where a numerical value of the UV index is equal to or greater than a predetermined value. The marker MK may be set according to an ultraviolet intensity (ultraviolet illuminance) instead of being set according to a numerical value of the UV index.

In each of the embodiments, the timepiece 4 or 4A functions as a notification device, and notifies a user of attention or warning according to a numerical value indicated by ultraviolet information (specifically, an UV index). However, any other configuration may be used, and, as described above, an external apparatus such as the measurement apparatus or 2A or the information terminal 5 may perform the notifications of attention and warning. On the other hand, such a notification device may not be included in the measurement system. The measurement apparatus 2 or 2A is not limited to a configuration of being mounted on the cap CP worn by a user and being used, and may be directly mounted on the user, and may be mounted on an object which is mounted on and carried by the user.

In each of the embodiments, in the timepiece 4 or 4A functioning as a display device, in a case where a numerical value of the UV index is equal to or smaller than 5 indicating that an ultraviolet intensity is moderate, the pointer P1 indicates the scales set in the right region in the small window 405, and, in a case where a numerical value of the UV index is equal to or greater than 6 indicating that an ultraviolet intensity is high, the pointer P1 indicates the scales set in the left region. However, this is only an example, and scales of 5 or smaller may be set on a lower part, and scales of 6 or greater may be set on an upper part. As mentioned above, a layout of scales pointed out by the pointer P1 indicating ultraviolet information may be changed as appropriate. A numerical value of the UV index may be indicated by using other hands such as the function hand P2 instead of the pointer P1, and other ultraviolet information such as an ultraviolet intensity may be indicated instead of a numerical value of the UV index.

What is claimed is:

1. An ultraviolet measurement system comprising:
    a measurement device that is configured to be portable by a user, and that is configured to measure ultraviolet information regarding an ultraviolet ray; and
    a display device that is configured to perform communication with the measurement device,
    wherein:
    one of the measurement device and the display device includes:
        a position acquisition unit that is configured to acquire position information indicating a position of either of the user and the measurement device, and
        a memory that is configured to store the ultraviolet information measured by the measurement device, in correlation with measurement position information that is position information of when the ultraviolet information is measured by the measurement device among pieces of position information acquired by the position acquisition unit, and
    the display device displays first information about the ultraviolet information and second information about the measurement position information.

2. The ultraviolet measurement system according to claim 1, wherein the display device displays an ultraviolet information image that corresponds to the ultraviolet information measured at a measurement position, the ultraviolet information image being set at a position on an image adjacent to the measurement position information, which indicates the measurement position in a map.

3. The ultraviolet measurement system according to claim 2, wherein the ultraviolet information image set in the image is a marker that differs depending on a numerical value indicated by the ultraviolet information.

4. The ultraviolet measurement system according to claim 1, wherein the memory stores the ultraviolet information in correlation with the measurement position information in a case where a numerical value indicated by the ultraviolet information is equal to or greater than a memory threshold value.

5. The ultraviolet measurement system according to claim 1, further comprising a notification device that sends a notification to the user in a case where a numerical value indicated by the ultraviolet information is equal to or greater than a notification threshold value.

6. The ultraviolet measurement system according to claim 5, wherein the notification device is further configured to continuously send the notification to the user in a case where a period in which the numerical value is equal to or greater than the notification threshold value is a predetermined period or more.

7. The ultraviolet measurement system according to claim 5, wherein the notification device is mounted on a wearable apparatus configured to be worn by the user, and the notification device being configured to send the notification to the user by causing a vibration.

8. The ultraviolet measurement system according to claim 1, wherein the display device includes a pointer indicating a numerical value indicated by the ultraviolet information.

9. The ultraviolet measurement system according to claim 8,
wherein:
the display device includes a dial pointed out by the pointer, and
the pointer points out portions opposite to each other in the dial in a case where a numerical value indicated by the ultraviolet information indicates that a degree of danger to the user is high and a case where a numerical value indicated by the ultraviolet information indicates that the degree of danger to the user is low.

10. The ultraviolet measurement system according to claim 8,
wherein:
the display device includes a timepiece that is configured to perform communication with the measurement device, and that is configured to be worn by the user, and
the timepiece includes the pointer.

11. The ultraviolet measurement system according to claim 1, wherein the display device includes the position acquisition unit and the memory.

12. An ultraviolet measurement system comprising:
a measurement device that is configured to be portable by a user, and is configured to measure ultraviolet information regarding an ultraviolet ray;
a position acquisition device that is configured to acquire position information indicating a position of either of the user and the measurement device;
a memory that is configured to store the ultraviolet information measured by the measurement device, in correlation with measurement position information that is position information of when the ultraviolet information is measured by the measurement device among pieces of position information acquired by the position acquisition device; and
a display device that displays first information about the ultraviolet information and second information about the measurement position information.

13. An ultraviolet measurement system comprising:
a measurement device that is configured to be portable by a user, and that is configured to measure ultraviolet information regarding an ultraviolet ray; and
a display device that is configured to perform communication with the measurement device,
wherein:
one of the measurement device and the display device includes:
a position acquisition unit that is configured to acquire position information indicating a position of either of the user and the measurement device, and
a memory that is configured to store the ultraviolet information measured by the measurement device, in correlation with measurement position information that is position information of when the ultraviolet information is measured by the measurement device among pieces of position information acquired by the position acquisition unit,
the display device displays information based on the ultraviolet information and the measurement position information, and
the display device includes a pointer indicating a numerical value indicated by the ultraviolet information.

* * * * *